United States Patent [19]

Kahn

[11] 4,344,326
[45] Aug. 17, 1982

[54] NON-DESTRUCTIVE TESTING OF A LAMINATED CERAMIC CAPACITOR

[75] Inventor: Sherwin R. Kahn, South Brunswick Township, Middlesex County, N.J.

[73] Assignee: Western Electric Company, Inc., New York, N.Y.

[21] Appl. No.: 171,585

[22] Filed: Jul. 23, 1980

[51] Int. Cl.³ .............................................. G01N 29/04
[52] U.S. Cl. ......................................... 73/587; 73/801
[58] Field of Search .................. 73/587, 588, 801, 799

[56] References Cited

U.S. PATENT DOCUMENTS

| | | | |
|---|---|---|---|
| 3,593,048 | 7/1971 | Dunegan et al. | 310/319 |
| 3,919,883 | 11/1975 | Nakamura et al. | 73/587 |
| 3,924,456 | 12/1975 | Vahaviolos | 73/587 |
| 4,075,886 | 2/1978 | Barker | 73/801 |
| 4,086,817 | 5/1978 | Jon et al. | 73/587 |

FOREIGN PATENT DOCUMENTS 1348086  3/1974  United Kingdom .

OTHER PUBLICATIONS

"Real Time Detection of Microcracks in Brittle Materials Using Stress Wave Emission (SWE)," *IEEE Transactions on Parts, Hybrids, and Packaging*, vol. PHP-10, No. 3, Sep. 1974, pp. 152-159.
"Western Electric Reports: Listening to the Cry of Materials Under Stress," *IEEE Spectrum*, May, 1975, p. 19.
"Forecasting Failures with Acoustic Emission," *Machine Design*, Jun. 14, 1973, pp. 132-137.
"Stress Wave Emission: Defining Its Capabilities," *Metals and Materials*, Mar. 1976, pp. 35-37.

Primary Examiner—Anthony V. Ciarlante
Attorney, Agent, or Firm—D. J. Kirk

[57] ABSTRACT

This disclosure is directed to techniques for proof testing a laminated ceramic capacitor chip (10) by placing the capacitor on a planar base (26) and applying a load thereto in a direction perpendicular to the laminations. The load is applied by a compliant ram (27) and acoustic emissions emanating from the capacitor (10) pass through the ram to a transducer (28) mounted thereon. The acoustic emissions are converted to electrical signals by the transducer (28) and are forwarded to processing circuitry (29) to compare the acoustic emission signals to previously developed signals from stressed physically acceptable capacitors (10) to determine the acceptability thereof.

11 Claims, 10 Drawing Figures

NON-DESTRUCTIVE TESTING OF A LAMINATED CERAMIC CAPACITOR

TECHNICAL FIELD

This invention relates to testing of capacitors. In particular, the invention is directed to proof testing of laminated ceramic capacitors using Acoustic Emission (AE) techniques.

BACKGROUND OF THE INVENTION

The reduction in size of electronic equipment achieved through the advancement of integrated circuit technology has dictated the development of smaller capacitors with sufficient capacitance for use in coupling and bypass applications. Capacitors using ferroelectric ceramic as the dielectric material can achieve a very high capacitance per unit volume due to its high permittivity. Moreover, ceramic capacitors can be manufactured very economically in a wide range of capacitance values and working voltages.

A particular type of capacitor referred to as a monolithic multilayer ceramic capacitor is fabricated by alternating layers of metal and ceramic material in a simple parallel plate arrangement. The capacity of such a device being a function of the number and surface area of the metallic layers (electrodes), their separation, and the permittivity of the ceramic (dielectric). Literally millions of such devices are provided each year by capacitor manufacturers.

Unfortunately, during the fabrication of such capacitors defects may be formed therein. Defects such as cracked ceramic, voids and delaminations of the layers have been found by destructively sectioning the capacitor after completion of the fabrication steps. Such mechanical defects are not always detected in standard electrical tests resulting in inferior product being placed in the field.

In view of the high production of such capacitors it would be most desirable to have a test procedure capable of detecting such defective capacitors early in the fabrication thereof and removing them from further processing, resulting in substantial cost savings. Additionally, service maintenance costs may be significantly decreased by reducing the number of capacitor field failures.

The present technique for detecting defects in multilayer ceramic capacitors is by sample lot evaluation. A small number of capacitors are withdrawn from a production lot, mounted in epoxy, sectioned and microscopically examined. This procedure is most time consuming and defects are judged by a technician based upon a subjective comparison to a predetermined scale. Typically, less than 100 capacitors out of several hundred thousand are tested using such techniques. Such a small sample may not be statistically significant.

Efforts have been made to replace the sectioning technique with non-destructive methods capable of examining a much larger sample of capacitors. Radiography and ultrasonic techniques have been attempted. However, radiography, as well as ultrasonics are both expensive techniques and not amenable to production line volume testing.

The most promising approach to the problem of finding physical defects in multilayer ceramic capacitors has been Acoustic Emission (AE) testing. AE testing is a well known technique and is described in U.S. Pat. No. 4,086,817 to Jon et al. which issued on May 2, 1978 and which is assigned to the instant assignee. AE may be defined as elastic waves which are characterized by low amplitude, short duration and fast rise time signals which are propogated in a structure as the result of an applied stress. The Jon patent is directed to detecting such signals, and operating thereon, to determine the quality of welds.

The use of AE as it relates to testing ceramic capacitors is based upon the premise that defects, such as cracks and delaminations, will propagate with the release of acoustic energy when an external stress is applied to a defective capacitor. The AE signal would then be detected and processed to determine the extent, if any, of physical defects therein.

Various attempts have been made to determine a stressing configuration capable of causing the defects to propagate in order to produce an AE signal representative of defects in the capacitor under test. Initially thermal shocking of a barium titanate ceramic laminated capacitor was thought to have promise to induce sufficient stress therein. However, experiments using a high sensitivity piezoelectric transducer revealed insignificant AE activity upon contact of the capacitor with a 750 F heated probe or immersion in a 500 F fluid.

A more predictable stress was obtained by bending the capacitor chips in a three-point bending fixture. The peak load (6.0 Kg) was chosen sufficiently below the average fracture strength of the capacitors so that the acceptable capacitors were not broken. However, no correlation was found between the severity of internal defects and the resultant AE signal in the sample tested. It appears that the relatively low load at which a good capacitor can be damaged is a serious disadvantage in this loading scheme.

In order to allow the use of larger loads, a capacitor under test was held in a vertical position and a load applied to the edge thereof, parallel to the laminations, by a steel ram. In this configuration of compression, the capacitor can tolerate much higher loads (e.g., 100 Kg) without damaging a good unit.

This parallel loading configuration resulted in capacitors exhibiting a very high AE signal when the capacitor had extensive internal physical damage therein and a very low AE signal when the capacitors were defect free. However, capacitors yielding a low to moderate AE signal gave ambiguous results for a substantial number of the capacitors tested.

Accordingly, it should be clear that the need exists for a non-destructive technique for unambiguously determining the physical acceptability of laminated ceramic capacitors.

SUMMARY OF THE INVENTION

The instant method overcomes the foregoing problems associated with testing a substantially planar capacitor having alternate laminations of metal and ceramic material by placing the capacitor on a planar base and applying a load thereto in a direction substantially perpendicular to the laminations. Acoustic emission signals emanating from the capacitor during the application of the load are monitored and compared to previously developed acoustic emission signals from physically acceptable capacitors to determine the acceptability thereof.

Additionally, it has been found that a compliant ram can be used to impress a load on the capacitor. Such a ram applies a more uniform load over the relatively uneven surface of the ceramic capacitor chip while transmitting AE signals therethrough to a transducer affixed thereon.

DETAILED DESCRIPTION

Figure 1:
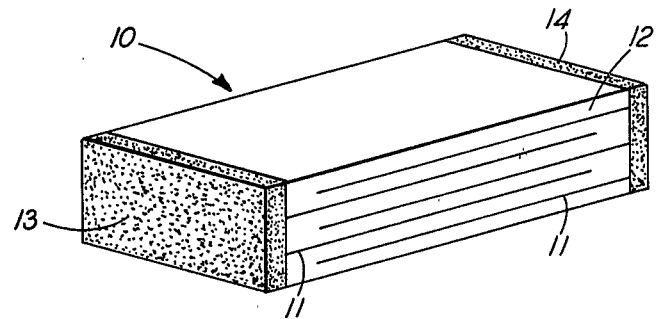
FIG. 1 is a schematic view of a laminated ceramic capacitor.

FIG. 1 depicts a laminated ceramic chip capacitor which is generally indicated by the numeral 10. The capacitor 10 is fabricated by alternating layers of metal electrodes 11 and ceramic 12 in a simple parallel plate arrangement. The metallic electrodes 11—11 are alternately connected to first and second electrical contact plates 13 and 14, respectively. Electrically conductive leads (not shown) are connected to the contact plates 13 and 14. The capacity of the capacitor 10 is a function of the number of the electrodes 11, their separation and the permittivity of the ceramic 12 which acts as a dielectric.

Typically, in fabricating a capacitor 10, finely powdered ceramic (e.g., doped barium titanate) is blended, calcined, and then mixed with organic binders to form a slurry which is then slip cast into a continuous tape approximately six inches wide. A liquid mixture (e.g., silver-palladium or the like) is silk-screened on sheets of unfired ("green") ceramic 12 cut from the continuous tape, to form the electrodes 11—11 thereon. These sheets are stacked in proper registration to obtain capacitors 10—10 having the desired value of capacitance and are then bonded together under pressure in a laminating press. Individual capacitors 10—10 are diced from the large laminated sheets, preheated to drive out the organic material, and then kiln fired to form a monolithic block or chip. Each capacitor 10 is completed by applying a frit (e.g., silver) to form the electrical contact end plates 13 and 14, affixing conductive leads thereto and molding the chip in plastic.

Figure 2:
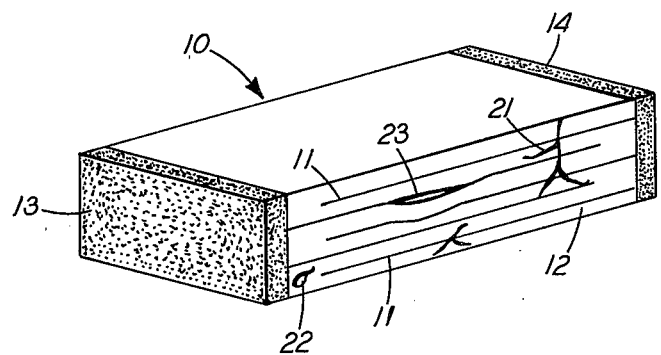
FIG. 2 is a schematic view of a laminated ceramic capacitor with various defects indicated therein.

It is likely that every laminated ceramic capacitor 10 has small physical flaws which do not degrade the performance of the capacitor in any way (such capacitors are nominally termed "defect free" herein). However, when such flaws, which are induced in the capacitor 10 due to undesirable variations in process conditions during manufacturing, are sufficiently large or numerous, the long term reliability of the capacitor is effected. Failure due to low insulation resistance or short circuiting has, in many cases, been linked to three types of physical defects: cracks 21, voids 22 or delaminations 23 as shown in FIG. 2.

Delaminations 23, which are separations between one of the electrodes 12—12 and a ceramic layer 13, are the most severe defects in the laminated ceramic chip capacitor 10. Delaminations 23 may vary in size from a few thousandths of an inch or less with very little ceramic displacement to total separation of an entire electrode 11 with severe disruption and cracking of the surrounding ceramic material. The most likely cause of delamination is too rapid release of vapor when organic materials are driven off during the preheating and firing steps. This evolution of gas may be sufficiently forceful to separate the electrode 11 from the ceramic 12 and crack the ceramic. In severe cases bits of broken metallization may be displaced in the ceramic 12. Additionally, delaminations 23 can also result from foreign material entering the capacitor 10 during the fabrication process.

Figure 3:
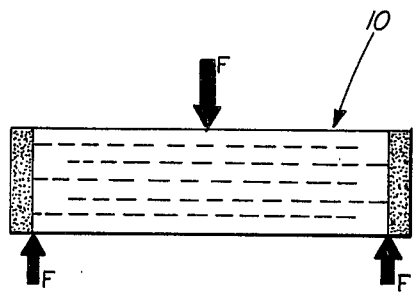
FIGS. 3 and 4 depict the instant capacitors being loaded in three point bending and parallel stressing, respectively.
Figure 4:
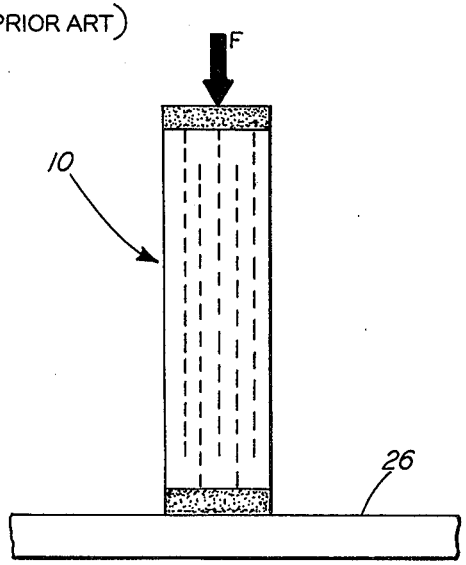

As hereinbefore indicated, the use of AE techniques in testing capacitors 10 have been tried using three point bending and applying a force (see arrows) parallel to the laminations as shown in FIGS. 3 and 4, respectively. Such techniques have not been successful for the reasons previously mentioned.

Figure 5:
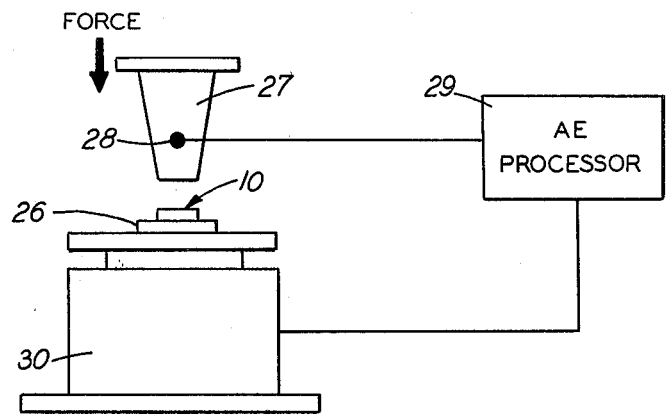
FIG. 5 is a diagrammatic representation of the proof testing apparatus incorporating the instant inventive concepts therein.

The instant technique, which overcomes the foregoing problems, is depicted schematically in FIG. 5. A capacitor 10 is placed on a planar base 26 and a ram 27, having an AE transducer 28 affixed thereto, applies a force in a direction perpendicular to the laminations of the capacitor. Any AE signals emanating from the capacitor 10 under test will be transmitted through the ram 27, detected by the transducer 28 and forwarded to an AE processor 29. Additionally, a load cell 30 positioned under the base 26 is also electrically connected to the AE processor 29. With this test configuration, no special fixturing is required to hold the capacitor 10 under test in a critical preferred position; the acoustic path is precisely reproducible, the load is applied over a relatively large surface area, and any flaws present are at most the thickness of the capacitor 10 from the surface of the application of the load.

A perfectly monolithic ceramic capacitor 10, properly laminated and containing no voids 22, cracks 21 or delaminations 23 should be capable of supporting a large, uniform, compressive load on a major surface thereof without inducing any damage therein since ceramic exhibits very high strength in compression. A delamination 23, however, will significantly reduce the ability of the capacitor 10 to withstand such a load. A compressive load applied to the face of a capacitor 10 containing delaminations 23 therein will cause bending and tension in the individual delaminated layers. If the applied load is sufficiently large, these forces may cause the delaminated ceramic to crack.

In both cases, acoustic energy will be emitted which can be detected, quantified, and used as an indication of the presence and the severity of the physical defects. With the load applied to the face of the capacitor 10, as shown in FIG. 5, the body of the capacitor 10 is free of bending moments. Hence, large loads may be applied to obtain good sensitivity to small, but significant, defects without the danger of fracturing or otherwise damaging good capacitors 10.

Typical AE processing equipment 29 is described in articles titled ACOUSTIC EMISSION DETECTION, PARTS I AND II, by Kahn et al., in The Western Electric Engineer, pages 3 to 19, October 1979 which is hereby incorporated by reference. Various types of AE signal processing such as peak detection, event counting and ringdown counting may be used to process the acoustic signals emanating from the laminated capacitor during the application of the load.

Figure 7:
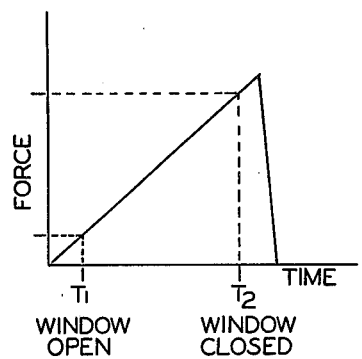
FIG. 7 is a curve of time versus force applied to the capacitor under test.
Figure 8:
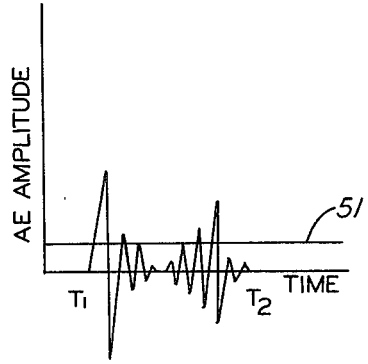
FIG. 8 is a general cure of AE amplitude versus time.
Figure 6:
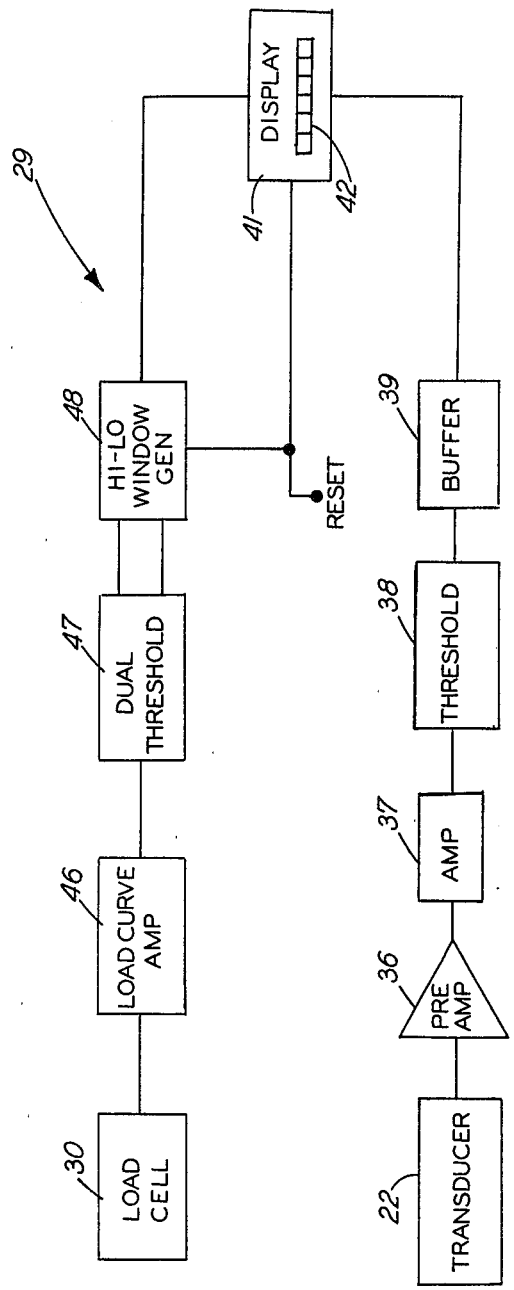
FIG. 6 is a block diagram of AE processing apparatus used to implement the instant invention.

The particular system used in an exemplary embodiment is shown in block diagram form in FIG. 6. AE data is only processed during the time window from times $T_1$ to $T_2$ (see FIG. 7) to eliminate spurious signals, due to the initial contact of the ram 27 with the capacitor 10 and due to lift-off of the ram at the end of stressing. During this time window the AE signal processor 29 counts the number of excursions of the detected AE signal above a preset threshold 51 as shown in FIG. 8.

The raw AE signal is detected by the transducer 22 which is a 1 MHz resonant, differential transducer such as that shown in U.S. Pat. No. 3,593,048. The output signal from the transducer 22 is forwarded to a low noise broadbend amplifier 36 (100 kHz–2 MHz) which amplifies the output signal by 40 db. The signal is then further amplified by 40 db by an amplifier 37. The amplified signal is then compared to a preset threshold in a threshold circuit 38 which is set at a level (e.g., 350 mv) sufficiently above the noise on the amplified AE signal to prevent noise spikes from being mistaken for AE signals. Each time the incoming AE signal exceeds the preset level a pulse is forwarded to a buffer circuit 39 where they are subjected to a level shift which changes their amplitude to 5 volts to ensure their compatability with a digital display apparatus 41.

The display apparatus 41 has a display counter 42 which is activated by a gate pulse from the load cell 30 (FIG. 5). As the load is applied to the capacitor 10, a ramp voltage proportional to the load is generated and forwarded to a load curve amplifier 46, having a variable gain of 10 to 100, wherein voltage is amplified. The amplified signal is applied to the input of a dual threshold circuit 47.

As the ramped voltage from the load cell 30 increases, it reaches the first or low threshold setting of 250 mv corresponding to a load of approximately 2 kg. This level was chosen to eliminate possible noise generated when the ram 27 contacts the capacitor 10, seating it on the base 26. At this point, the low level comparator switches causing a high-going low transition to occur at the low input of a high-low window generator 48. This change causes a one shot to fire and latch a high-low flip-flop initiating the display gate pulse. At this point, the digital display 42 is enabled and can record a pulse count from the buffer 39 representing threshold excursion of the AE ringdown signal above the preset threshold 51 emanating from the capacitor 10 under test.

As the load is applied by the ram 27, the ramped voltage will reach a second or high threshold setting of 700 mv corresponding to a load of approximately 18 kg. When this level is exceeded, the high level comparator switches causing a transition to occur at the high input of the high-low window generator circuit 48. This resets the high-low flip-flop, terminating the display gate pulse which prevents the recordation of additional signal which may occur after the test has been completed. The count which appears in the display counter 42 corresponds to the number of AE threshold crossings caused by a load rising from 2 to 18 kg.

In order to determine ranges of AE counts that are acceptable from a physical standpoint capacitors 10 were placed on a thick resilient base 26 (e.g., Teflon—a registered trademark of E. I. Dupont De Nemours Co.), as shown in FIG. 5 and a load rising substantially linearly (see FIG. 7) to a maximum of 4 kg was applied. Grossly delaminated capacitors 10 shattered at loads under 4 kg while good devices exhibited at AE count under 100. In a sample of 34 capacitors 10, processed without preheating in order to induce delaminations, 50% of the sample exhibited an AE count above 493 while the other 50% had counts at 78 or below. In a sample of 28 capacitors 10, processed with preheating to reduce the incidence of delaminations, no capacitor exhibited over 75 counts. This data is summarized in Table A:

TABLE A

| PREHEATED | NON-PREHEATED |
|---|---|
| (AE Count) | (AE Count) |
| 1 (15) | 1 (10) |
| 2 (2) | 2 |
| 3 | 5 |
| 4 (2) | 24 |
| 5 | 62* |
| 15 | 66 |
| 20 | 77* |
| 26 | 78* |
| 28 | 493* |
| 37* | 909* |
| 65* | 1,401* |
| 75* | 2,088* |
| | 3,761* |
| | 4,407* |
| | 4,683 |
| | 38,929 |
| | 72,350 |
| | 53,217 |
| | 101,808 |
| | 115,281 |
| | 110,520 |

( ) Number of occurrences
*Sectioned

The observation that the relatively defect free preheated capacitors 10 all yielded 75 counts or fewer, coupled with the clear separation of the non-preheated capacitors into two distinct count ranges (less than 78 counts and greater than 493 counts) strongly suggests that the low count range should be associated with good product while the high range is indicative of poor product.

To verify the correlation between AE counts and internal physical defects suggested by the data in Table A, it was necessary to examine the test capacitors 10 by microsectioning. Sectioning of 15% of the preheated capacitors 10 tested (less than 75 counts) revealed no defects. Twenty-five percent of the non-preheated capacitors 10 were sectioned. With the exception of one capacitor 10 exhibiting 493 counts, all the samples taken from the upper count group had delaminations while no defects were found in capacitors from the low count group. No defect free capacitors 10 were found to have a higher count than a defective capacitor.

It should be clear from the foregoing that by monitoring and counting AE signals passing above a predetermined threshold during the application of a load orthogonal to the laminations, the acceptability of the capacitor 10 may be determined by comparing the monitored counts to empirically developed ranges of counts associated with acceptable capacitors.

As hereinbefore indicated the base 26 may advantageously be made of a compliant Teflon material such to accommodate the relatively rough surface of the ceramic capacitor 10 in order to apply a more uniform load thereto. Additionally, the instant apparatus may incorporate a ram 27 made of similar compliant material. Heretofore, rams 27 used to apply a force to an object, during AE testing, were made of metal. In particular, when an AE transducer is attached to the ram 27, the ram becomes an integral part of the AE transmission path between the capacitor 10 and the AE transducer. It has been a widely held belief of those skilled in the AE art that plastics and other soft materials should be kept out of the AE transmission path since their acoustic attenuation is higher than that of metals. However, it has been discovered that the use of compliant Teflon material shows little attenuation in the frequency range of interest (less than 3 db under 500 KHz).

In the instant exemplary embodiment the capacitor 10 was approximately 5 by 6 by 1 mm and the compliant Teflon ram 27 was between 55 to 65 durometers on the Shore D scale. The ram 27 may have a different hardness depending on the parameters of the capacitor 10 (e.g., size, material, etc.).

Figure 9:
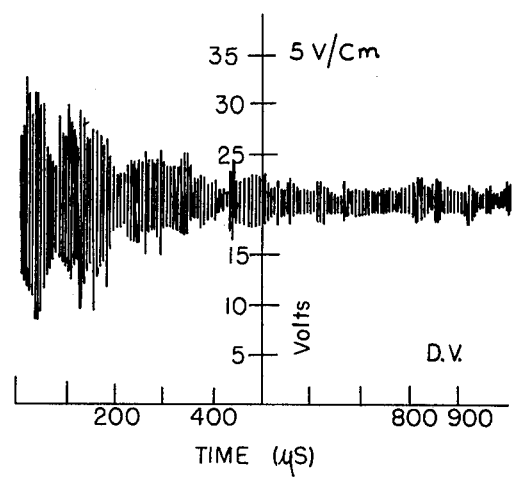
FIGS. 9 and 10 are curves of AE ringdown signals for a compliant and a steel ram, respectively.
Figure 10:
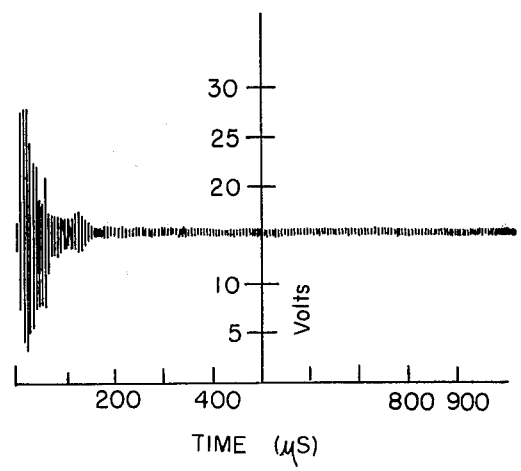

Further, AE testing using a compliant Teflon ram 27 unexpectedly resulted in shorter ringdown times of the AE signal as indicated in FIG. 9 (steel ram) and FIG. 10 (Teflon ram). As can be seen the ringdown tends to be almost an order of magnitude shorter for the compliant ram 27 than for a similarly shaped steel ram. Advantageously, with the shorter ringdown time, there is less likelihood of overlapping AE events even at higher stressing rates. Accordingly, throughput may be increased substantially.

It is to be understood that the embodiments described herein are merely illustrative of the principles of the invention. Various modifications may be made thereto by persons skilled in the art which will embody the principles of the invention and fall within the spirit and scope thereof.

What is claimed is:

1. A method of testing a substantially planar capacitor having alternate laminations of metal and ceramic material, comprising the steps of:

placing the capacitor on a planar base;

applying a load to the laminated capacitor in a direction perpendicular to the laminations;

monitoring acoustic emission signals emanating from the capacitor during the application of the load; and comparing the acoustic emission signals to previously developed acousic emission signals from physically acceptable capacitors to determine the acceptability of the capacitor.

2. The method as set forth in claim 1, wherein:
    the load is applied in a substantially linearly increasing fashion.

3. The method as set forth in claim 2 wherein:
    the linearly increasing load is directly proportional to parameters of the ceramic layers.

4. The method as set forth in claim 3 wherein:
    the parameters are thickness and density of the ceramic material.

5. The method as set forth in claim 1, wherein:
    the load is applied to the capacitor through a compliant ram.

6. The method as set forth in claim 4 or 5 wherein:
    the capacitor is placed on a compliant base during the application of the linearly increasing load.

7. The method as set forth in claim 1 wherein:
    the monitored acoustic emission signals passing above a predetermined threshold, during the application of the load, are counted; and the count is compared to empirically developed ranges of counts to determine the acceptability of the capacitor.

8. A method of testing a substantially planar capacitor having alternate laminations of metal and ceramic material, comprising the steps of:

placing the capacitor on a planar base;

applying a load to the laminated capacitor with a compliant ram having an acoustic emission transducer applied thereto, the ram being compliant to the extent that it assumes an impression of at least a portion of the capacitor being tested; and monitoring acoustic emission signals emanating from the capacitor and transmitted by the compliant ram to the transducer.

9. The method as set forth in claim 8, which further comprises:

comparing the acoustic emission signals emanating from the capacitor with previously developed acoustic emission signals from physically acceptable capacitors to determine the acceptability of the capacitor under test.

10. An apparatus for applying a force to an article in order to monitor acoustic emissions emanating therefrom, comprising:

a compliant ram having an acoustic emission transducer fixedly mounted thereon to monitor acoustic emission signals emanating from the article as the ram applies a load thereto, the ram being compliant to the extent that it assumes an impression of at least a portion of the article being tested.

11. The apparatus as set forth in claim 10, wherein the article is placed on a substantially planar compliant base.

* * * * *